United States Patent
Jiang

(10) Patent No.: US 11,359,193 B2
(45) Date of Patent: Jun. 14, 2022

(54) PREPARATION METHOD FOR IN-SITU HYBRIDIZATION PROBE

(71) Applicant: DIAGLOGIC BIOLABS (XIAMEN) CO., LTD., Fujian (CN)

(72) Inventor: Xiaoqun Jiang, Fujian (CN)

(73) Assignee: DIAGLOGIC BIOLABS (XIAMEN) CO., LTD., Fujian (CN)

( * ) Notice: Subject to any disclaimer, the term of this patent is extended or adjusted under 35 U.S.C. 154(b) by 28 days.

(21) Appl. No.: 16/758,283

(22) PCT Filed: Aug. 9, 2018

(86) PCT No.: PCT/CN2018/099530
§ 371 (c)(1),
(2) Date: Apr. 22, 2020

(87) PCT Pub. No.: WO2019/080595
PCT Pub. Date: May 2, 2019

(65) Prior Publication Data
US 2020/0248170 A1    Aug. 6, 2020

(30) Foreign Application Priority Data
Oct. 24, 2017   (CN) .......................... 201711000583.8

(51) Int. Cl.
C12N 15/10    (2006.01)
C12Q 1/6827   (2018.01)
C12Q 1/6874   (2018.01)

(52) U.S. Cl.
CPC .......... *C12N 15/102* (2013.01); *C12Q 1/6827* (2013.01); *C12Q 1/6874* (2013.01); *C12Q 2600/156* (2013.01); *C12Q 2600/158* (2013.01)

(58) Field of Classification Search
CPC ............ C12Q 1/6806; C12Q 2521/301; C12Q 2521/501; C12Q 2523/301; C12Q 2527/101; C12Q 1/6827; C12Q 1/6841; C12Q 1/6874; C12Q 2600/156; C12Q 2600/158; C12N 15/10; C12N 15/102
See application file for complete search history.

(56) References Cited

U.S. PATENT DOCUMENTS

2016/0215334 A1*   7/2016   Russell ................ C12Q 1/6876

FOREIGN PATENT DOCUMENTS

| CN | 1384208 A | 12/2002 |
| CN | 107208091 A | 9/2017 |
| CN | 107603971 A | 1/2018 |

OTHER PUBLICATIONS

Li, Yan et al., "A Novel Method for High Efficiency Amplification of Short DNA Fragments", Journal of Capital Medical University, vol. 32, Issue No. 1, Feb. 28, 2011, pp. 121-124. Abstract only.

* cited by examiner

Primary Examiner — Cynthia B Wilder
(74) Attorney, Agent, or Firm — Muncy, Geissler, Olds & Lowe, P.C.

(57) ABSTRACT

A preparation method for in-situ hybridization probes as follows: fragmenting objective DNAs, recovering 150-600 bp fragments, and after an enzyme modification, ligating, at intervals, the fragments with DNA adaptors containing restriction enzyme site sequences to large DNA loops and long chains; obtaining and labeling a large amount of DNAs in step A or B: A. isothermal amplifying, adding a single nucleotide substrate with a marker when amplifying, to obtain a DNA product with a marker; or B. isothermal amplifying, doping a single nucleotide substrate with a marker to the obtained product with a nick translation or random primer method, to obtain a DNA product with a marker; and digesting the DNA product with the marker by using corresponding restriction enzyme, to obtain in-situ hybridization probes with lengths of 150-600 bp. The method of the present invention accurately controls length range of the probes, reduces production cost, and improves product quality.

6 Claims, 3 Drawing Sheets

PREPARATION METHOD FOR IN-SITU HYBRIDIZATION PROBE

TECHNICAL FIELD

The present invention relates to the field of biotechnology DNA probes, and in particular, to a preparation method for in-situ hybridization probes.

BACKGROUND ART

DNA hybridization is a procedure of denaturing both DNA fragments with markers (i.e. DNA probes) and DNAs having the same base sequences as probes (i.e. target sequences) to single chains and then form double chains by coupling with each other in a renaturing procedure based on the base complementary principle (i.e. DNA hybridization). Detection of the markers on the probes is used for qualitative and quantitative measurements of the target sequences. The probe is usually in a solution and is in a mobile phase, while the target sequence is usually in a stationary phase. According to a difference of the state and carrier where the target sequence is on, the hybridization is defined as, for example, Southern hybridization for target DNA on film, Comparative Genomic Hybridization (CGH) for target DNA on chips, in-situ hybridization for target DNA on cells or tissue sections, liquid phase hybridization for target chromosome or cells in solution or microfluidic system and the like. In commercial applications, it is necessary to prepare DNA probes in a large amount, and the preparation of in-situ hybridization probes will be described below as an example.

ISH stands for In-Situ Hybridization and FISH stands for Fluorescence In-Situ Hybridization. ISH is a molecular cytogenetic technique of detecting DNAs (or genes) or chromosome numbers or position changes in specimens by hybridizing small DNA fragments with markers, namely, hybridization probes, with DNA homologous target sequences in tissues or cells and detecting signals generated from the markers. The in-situ hybridization probe is a nucleotide sequence (a small fragment of DNA) with a marker, and there is a stricter requirement for its length. If it is too long, it is not easy to penetrate to the position where the target sequence is, and if it is too short, specificity is not sufficient and an unspecific signal or a high background is generated. FISH is to hybridize target DNA in tissues or cells with probes labeled with fluorescence, and to record and analyze results by observing and counting numbers and distributions of various fluorescence signals under a fluorescence microscope. It combines high sensitivity and intuitiveness of the fluorescence signals and positioning of the in-situ hybridization in the cells and tissues, so as to detect and diagnose cell or tissue specimens with abnormal chromosome or gene, providing an accurate basis for classification and prognosis of gene related diseases, and showing obvious advantages as compared with some traditional techniques. (1. Raap A K: Advances in fluorescence in situ hybridization. Mutat Res 400: 287-298 (1998). 2. Raap A K: Overview of fluorescence in situ hybridization techniques for molecular cytogenetics. Curr Protoc Cytom Chapter 8: Unit 8.1 (2001). 3. Wang N: Methodologies in cancer cytogenetics and molecular cytogenetics. Am J Med Genet. 115: 118-124 (2002). 4. Wolff D J, Bagg A, Cooley L D, Dewald G W, Hirsch B A, et al: Guidance for fluorescence in situ hybridization testing in hematologic disorders. J Mol Diagn 9: 134-143 (2007).

At present, the in-situ hybridization probes in clinical application for detecting gene amplification, gene deletion and chromosome translocation are usually prepared by using a large amount of BAC DNAs as templates, and the probe labeling methods are usually nick translation or random primering (for example, an invention of DA AN GENE CO LTD SUN YAT SEN titled as "PREPARATION METHOD FOR PROBES RELATED TO BREAST CANCER MOLECULAR MARKERS AND APPLICATION THEREOF", with Chinese Application No. 201010284090.3; and an invention of BEIJING GP MEDICAL TECHNOLOGIES LTD titled as "DETECTION AGENT FOR DETECTING PROSTATE CANCER AND APPLICATION THEREOF", with Chinese Application No. 201010113005.7). The two methods adopted for preparing the probes both need to prepare a large amount of BAC DNAs, the cost is higher, and the marking methods are not easy to accurately control the length range of the probes, causing the products produced in different batches to have larger variations (bad repeatability) and unstable product performance indexes.

SUMMARY

The present invention aims to provide a preparation method of DNA in situ hybridization probes to solve the problems of high cost of large-scale preparation of in situ hybridization probes, difficult control of probe length range and unstable product quality.

To achieve the above purpose, the present invention provides a preparation method for DNA in-situ hybridization probes, characterized by including the following steps:

fragmenting and selective recovering of target DNAs: fragmenting the target DNAs, and selectively recovering 150-600 bp small fragments;

enzyme modification processing: performing an enzyme modification processing on two ends of 150-600 bp small DNA fragments, to make the two ends blunt, then 5' end phosphate added and 3' end dA added;

ligating into large loops and long chains: ligating the above processed small DNA fragments and DNA adaptors at intervals to form large DNA loops and long chains. The DNA adaptor has restriction enzyme site sequence, phosphate at 5' end and dT at 3' end;

obtaining and labeling of a large amount of DNAs:

A. isothermal amplifying, adding substrates with markers when amplifying, to obtain DNA products with the markers;

or B. isothermal amplifying, then doping a single nucleotide substrate with a marker to the obtained product by nick translation method or random primer method, to obtain a DNA product with the marker;

wherein the markers include direct markers and indirect markers; the direct markers are markers that can be detected by a detection system, including but not limited to radioactive isotopes, biotin, an antigen or a hapten such as digoxin and fluorescein; and the indirect markers are some chemical groups that cannot be detected by the detection system, these chemical groups including but not limited to aliphatic primary amine groups and thiols, and they need to be coupled with a direct marker (through a reaction group) with a corresponding reaction group, for example, aminoallyl (AA) and succinimidyl ester (SE) are coupled under alkaline condition, so as to label the direct marker onto DNA;

enzyme digesting: digesting the marker labeled DNA product with a DNA restriction enzyme corresponding to a base sequence of the above DNA adaptor, wherein a length range of the enzyme digested product is 150-600 bp;

obtaining a probe:

if the marker in the labeled DNA product is a direct marker, the obtained enzyme digested product being the in-situ hybridization probe; and if the marker in the labeled DNA product is an indirect marker, the obtained enzyme digested product being coupled with the direct marker having corresponding reactivity, thereby obtaining the in-situ hybridization probe.

Further, the obtained in-situ hybridization probe is further purified and quantified.

Further, the target DNAs are purified target DNAs.

Further, in the step A or B, the primer used when isothermal amplifying is an oligonucleotide of the adaptor sequence containing restriction enzyme site or oligonucleotides of random sequences.

Further, in the step A or B, the enzyme used when isothermal amplifying is a DNA polymerase having chain replacement activity.

Further, the enzyme used when isothermal amplifying is Phi29 DNA polymerase or Bst DNA polymerase large fragments.

Further, in the step A or B, the markers are direct markers or indirect markers.

The target DNAs are DNAs containing the sequences of probe target.

The inserted restriction enzyme site sequence within the adaptor in the present invention is based on a principle that by inserting a sequence it does not affect the enzyme digestion of DNA with doped markers, for example, doping dUTP with the marker, the enzyme cannot cut the DNA after T is replaced with U, and the sequences containing T and A should not be selected; and a principle that the inserted enzyme digesting site sequences are as few as possible in the objective sequences, to reduce an impact on a length range designed for the probe products.

A DNA polymerase having chain replacement activity adopted in the present invention (such as Phi29 DNA polymerase and Bst DNA polymerase large fragments) is a high-effective DNA polymerase, has special chain replacement and continuous synthetic characteristics, works at a constant temperature, and is often applied to large amount amplification of trace DNAs, such as preparation of complete genome sequencing sample from a single cell.

The present invention includes the following advantageous effects:

In the present invention, a small amount of target DNAs are used as starting materials, they are prepared to a small fragment library within the designed length range, and are ligated at intervals with DNA adaptors containing restriction enzyme site sequences to large DNA loops and long chains, a large amount of amplification is performed through Loop Mediated Isothermal Amplification (LAMP) (with respect to circular DNAs) and Multiple Displacement Amplification (MDA) (with respect to linear DNAs), the markers are doped when amplifying or subsequently the makers are doped with the nick translation method (or the random primer method and its variation), and then the marker labeled DNAs are cut by using restriction enzymes to restore to small fragments with fragment lengths of the original library, so as to obtain a large amount of probes within the designed length range. Compared with the technique of usually using BAC, plasmid or PCR products and the like directly as templates and adopting the nick translation method or the random primer method to label and prepare probes, the present invention ligates the library fragments of probes with the designed length at intervals with restriction enzyme site sequence to form large DNA loops and long chains as probe templates; uses the inserted restriction enzyme site sequence (or random sequences) as primer sequence; performs DNA isothermal amplification; and dopes a substrate with a marker to label DNAs when or after amplifying DNAs by adopting other methods, wherein the inserted restriction enzyme sites are the cut sites for the labeled DNAs to be cut into probes within the designed length range, thus providing a preparation method of producing a large amount of probes within the designed length range more conveniently, increasing production yield, accurately controlling the length range of the probes, reducing consumption of raw materials during the production, saving on cost, and improving performance indexes of products.

The in-situ hybridization probes prepared by adopting the method of the present invention may be applied to but not limited to in-situ hybridization of interphase or metaphase cell nucleus (in tissue sections or cells) or CGH chip hybridization. The existence or non-existence, number changes and position changes of specific genes or DNA fragments in a specific cell/cell population/tissue/plant/animal/human body can be known from analysis of the hybridization results, which is related to early detection and diagnosis of diseases, selection of drugs for treatment, or prognosis judgment.

DETAILED DESCRIPTION OF EMBODIMENTS

Figure 1:
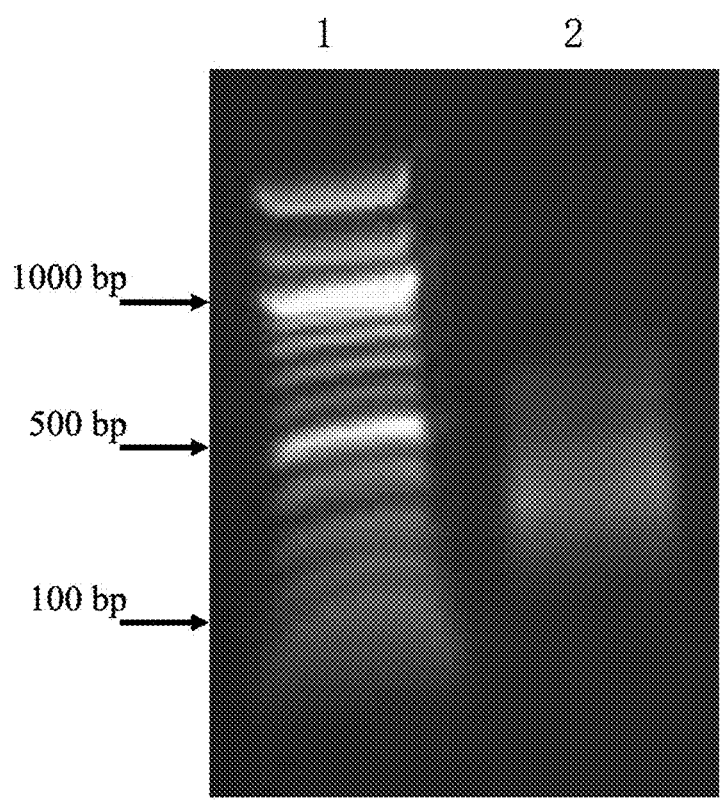
FIG. 1 is an agarose gel electrophoresis diagram of an HER2 gene detection FISH probe in Embodiment 2.

Embodiments of the present invention will be described in details below, and examples of the embodiments are shown in the accompanying drawings, wherein the same or similar reference signs indicate the same or similar components or components having the same or similar functions throughout. The embodiments described below with reference to the accompanying drawings are exemplary, and are intended to explain the present invention, but cannot be understood as limitations to the present invention. If specific techniques or conditions are not indicated in the embodiments, the techniques or conditions described in the literature in the art or according to the product instructions are performed. The used reagents or instruments that are not indicated with manufacturers are all conventional products commercially available.

A first preparation method for an in-situ hybridization probe of the present invention is as follows:

I. fragmenting and processing a purified target DNA to small fragments with a length of about 300 bp;

II. recovering small DNA fragments within the length range of 150-600 bp;

III. performing an enzyme modification processing on two ends of small DNA fragments recovered in step II, to make the two ends blunt, then the 5' end phosphate added and the 3' end dA added;

IV. under the action of DNA ligase, ligating the small DNA fragments (subjected to the enzyme modification in step III) and DNA adaptors (which have restriction enzyme site sequence, phosphate at 5' end and dA at 3' end) at intervals to form large DNA loops and long chains;

V. by adopting oligonucleotide of the adaptor sequence as a primer, performing LAMP and MDA on the large DNA loops and long chains obtained in step IV, and doping deoxyribonucleotide with a marker simultaneously, such as dUTP-fluorescein or aa-dUTP, to obtain DNA with the marker after amplification;

VI. performing an enzyme digesting on the above obtained DNA with the marker after amplification, by using a restriction enzyme corresponding to the inserted adaptor sequence, to obtain an enzyme digested product with the length range of 150-600 bp; and VII. purifying and quantifying the above obtained enzyme digested product to obtain the probe, completing preparation of the DNA hybridization probe.

The target DNA in step I is a double-stranded DNA, may be linear or circular, may be in a supercoil state, and may be continuous or may be nicked, and a source includes but is not limited to plasmid, BAC, YAC, PCR products, RT-PCR products, DNA enzyme digested products or ligated products, artificial amplification products and artificial synthetic products.

The ligation satisfies complementation between dT of the 3' end on the DNA adaptor and dA of a 3' end of the small DNA fragment.

In step V, if the doped marker is an indirect maker aa, it further needs to add a coupling step between steps VI and VII, and the direct marker is labeled on it.

A second preparation method for an in-situ hybridization probe of the present invention is the same as the above method except that the primer in the above step V is a random primer.

A third preparation method for an in-situ hybridization probe of the present invention is the same as the above two methods except for the following steps:

Step V. not doping the deoxyribonucleotide with the marker when performing isothermal amplifying;

Step VI. doping a single nucleotide substrate with a marker to the DNA obtained in step V with the nick translation method, labeling the DNA;

Step VII. digesting the marked DNA product by adopting a restriction enzyme corresponding to the enzyme digesting site on the adaptor, to obtain an enzyme digested product with the length range of 150-600 bp; and Step VIII. purifying and quantifying the above obtained enzyme digested product to obtain the probe, completing preparation of the DNA in-situ hybridization probe.

A fourth preparation method for an in-situ hybridization probe of the present invention is the same as the third preparation method for the in-situ hybridization probe except for the following step:

Step VI. doping the single nucleotide substrate with the marker to the DNA obtained in step V with random primer method, labeling the DNA.

A fifth preparation method for an in-situ hybridization probe of the present invention is the same as the fourth preparation method for the in-situ hybridization probe except for the following step:

Step VI. for the DNA obtained in step V, adopting oligonucleotide of the adaptor sequence as a primer to replace the random primer, labeling the DNA.

Embodiment 1: Preparation of Human Chromosome 17 Enumeration FISH Probe (CEN17)

I. Genomic DNA of a normal person (which is commercially available) is used as a template, a 0.85 kb PCR product of chromosome 17 centromeric α satellite repetitive sequence is obtained according to a method described in the article of Warburton et al. (Peter E. Warburton, Gillian M. Greig, Thomas Haaf, and Huntington F. Willard. PCR amplification of chromosome-specific alpha satellite DNA: definition of centromeric STS markers and polymorphic analysis. GENOMICS 11: 324-333 (1991)).

The PCR product is purified with the QIAquick™ PCR purification kit.

II. 1 μg of DNAs obtained in the above step are fragmented to a length of about 300 bp by using a focused ultrasonic method. Through 2% agarose gel electrophoresis with 100 bp DNA ladder as a reference, DNA fragments within the length range of 150-600 bp are cut from the gel and recovered with a gel extraction kit (QIAquick™ Gel Extraction Kit, Qiagen).

III. Enzyme modification processing: by adopting NEB-Next® Ultra End Repair/dA-Tailing Module of the New England Biolabs company, the ends of the DNA fragments recovered in step II are blunted according to operation steps of the instruction, the 5' ends thereof are phosphorylated, and dA is added at the 3' ends, and then the modified DNA fragments are recovered with a PCR Purification Kit (QIAquick™ PCR Purification Kit, Qiagen).

IV. Ligating into large loops and long chains: the adaptor, as below, containing DNA restriction enzyme Sac II site sequences is ligated with the modified DNA fragments recovered in step III.

The adaptor is double-stranded, and the 5' ends thereof are all phosphorylated, and the sequences are shown as follows:

5'-pCCGCGGT-3'

3'-TGGCGCCp-5'.

Steps of the ligation with the adaptor are as follows:

The following ligating system is adopted, a microcentrifuge tube is placed on an ice, 50 μl of the following reaction solution (a reaction volume may be expanded in proportion) is added, gently mixed by using a pipettor, briefly centrifuged, and then placed at 16° C. overnight.

| | |
|---|---|
| 10 times of T4 DNA ligase reaction buffer solution | 5 μl; |
| DNA fragments recovered in step VI | 100 ng; |
| Adaptor | 3 ng; |
| T4 DNA ligase | 50 u; |
| Deionized water | filling up to 50 μl. |

Purify and recover the ligated product with the QIAamp™ DNA Blood Kit of Qiagen. Non-ligated adaptor is removed. Measure the OD value of the purified DNA. A large-loop and long-chain DNA probe template is obtained.

V. Obtaining of a large amount of marked DNAs: the probe template DNAs obtained in step VI are amplified in a large amount while doping a marker dUTP-FITC (fluorescein isothiocyanate) (which may also be an indirect marker aa-dUTP. If it is so, it needs to add a coupling reaction with FITC SE after step VI. Please refer to the embodiments described later for details), the inserted sequence CCGCGGT is used as a primer, and the reaction system and procedure are as follows (the reaction volume may be increased in proportion):

| | |
|---|---|
| DNA probe template | 1 ng; |
| 10 times of buffer solution | 1.5 μl |
| Primer | 100 μM (final concentration in 15 μl) |
| Deionized water | adding up to 15 μl; |

Put it at 96° C. for 2 minutes and then at a room temperature for 10 minutes. Thereafter, it is placed on ice, the following components are then added so that the final volume is 50 μl, and they are mixed well:

| | |
|---|---|
| 10 times of buffer solution | 5 μl |
| DMSO | 2 μl |
| BSA | 2 μg |
| dNTP (dUTP-FITC:dTTP = 3:1) | 400 μM (final concentration in 50 μl of the reaction system) |
| Bst DNA polymerase, large fragments | 20 μ |
| Deionized water | adding up to 50 μl |

Then, they are placed at 60° C. for 6 hours, and then at 80° C. for 15 minutes.

The QIAamp™ DNA Blood Kit of Qiagen is adopted to perform purifying and recovering on the product. OD value is measured.

VI. Enzyme digesting: the produced obtained in step V is digested by the DNA restriction enzyme Sac II to obtain an enzyme digested product with a length range of 150-600 bp.

The enzyme digesting reaction system is (the reaction volume may be increased or reduced in proportion) as follows:

| | |
|---|---|
| Product obtained in step V | 100 μg |
| Sac II | 1000 u (unit) |
| Deionized water | reaching up to 1000 μl |

The above enzyme digesting reaction system is placed at 37° C. for 16 hours;

VII. The enzyme digested product is purified with a PCR purification kit (QIAquick™ PCR Purification Kit, Qiagen). Measure the OD value. A chromosome 17 enumeration FISH probe (CEN 17) labeled with green fluorescein FITC is obtained.

Embodiment 2: Preparation of Human Epidermal Growth Factor Receptor 2 (HER2) Gene Detection FISH Probe Embodiment 2 is different from the above Embodiment 1 in that the DNA is from BAC, the amplification and labeling are performed separately, a 6-base random primer (included in the kit used) is used when amplifying, after amplification, a marker is doped using nick translation method, and the doped marker is a direct maker or an indirect marker.

I. According to the position of HER2 gene on chromosome, a bacterial artificial chromosome (Bacterial Artificial Chromosome, BAC) clone: RP11-909L6 is purchased from the ThermoFisher Scientific company, wherein the HER2 gene and its adjacent chromosome DNAs are included, and the length thereof is about 185 kb.

An end sequencing method is adopted to sequence hundreds of bases at two ends of the BAC clone insertion. The sequencing result is compared with the known sequence in NCBI data base for verification.

II. 1 μg of BAC DNA is fragmented by using a focused ultrasonic method and the 150-600 bp DNA fragments are recovered, wherein the method is the same as that in Embodiment 1.

III. Enzyme modification processing: the method is the same as that in Embodiment 1.

IV. Ligating the DNA fragments recovered in step II and adaptor containing a DNA restriction enzyme Sma I site sequence;

The adaptor is double-stranded, and the 5' ends thereof are all phosphorylated. The sequences are shown as follows:

```
5'-pCCCGGGT-3'

3'-TGGGCCCp-5';
```

Ligating with the adaptor: the method is the same as that in Embodiment 1.

V. Obtaining of a large amount of DNAs: the DNA obtained in step IV is used as a template for a large amount of DNA amplification, the REPLI-g Single Cell Kit of Qiagen (the principle thereof being LAMP and MDA, adopting Phi29 DNA polymerase, and adopting 6-base oligonucleotides of random sequences as primer) is adopted to operate according to the instruction, and the amplified product is purified and recovered by adopting the QIAamp™ DNA Blood Kit of Qiagen.

VI. Labeling of the DNA: the amplified product obtained in step V is used as a template, and a direct marker dUTP-TAMRA™ (carboxytetramethylrhodamine) or an indirect marker aa-dUTP is doped by nick translation, wherein the method is as follows:

| | |
|---|---|
| Purified amplified product | 100 μg |
| dNTP (dUTP-FITC:dTTP = 3:1) | 0.2 mM (final concentration in the reaction system) |
| DNA polymerase I | 500 u |
| DNA enzyme I | 0.001 u |
| Deionized water | reaching up to 1000 μl |

The above mixture is placed at 30° C. for 16 hours; and Purify and recover the labeled products with the QIAamp™ DNA Blood Kits of Qiagen. Measure the OD value of the purified DNA.

VII. Enzyme digesting: the DNAs obtained in step VI are enzyme digested by restriction enzyme Sma I, to obtain an enzyme digested product with a length range of 150-600 bp.

The enzyme digesting reaction system is as follows:

| | |
|---|---|
| DNA | 100 μg |
| Sma I | 1000 u (unit) |
| Deionized water | reaching up to 1000 μl |

Incubate at 37° C. for 16 hours.

VIII. The PCR purification kit of Qiagen is adopted to purify the enzyme digested product obtained in step VII and measure the OD value. If the direct marker is doped in step VI, then the HER2 probe labeled with the orange-red fluorescent TAMRA™ is obtained; and if the indirect marker is doped in step VI, and then a step of IX is needed.

IX. Coupling between the aa doped in the DNA and TAMRA™ SE, and referring to the following paper or product instruction (the reaction volume may be correspondingly expanded in proportion):

W. Gregory Cox and Victoria L. Singer. Fluorescent DNA hybridization probe preparation using amine modification and reactive dye coupling. BIOTECHNIQUES 36: 114-122 (January, 2004).

X. After the product is purified through ethanol precipitation, the OD value is measured, and the HER2 probe labeled with the orange-red fluorescent TAMRA™ is obtained.

Explanation about Embodiment 2: the characteristics of the nick translation method lie in rapidness, convenience, homogeneity of labeling, high specificity, and higher labeling rate of probe than that of probe labeled with the Bst DNA polymerase; and the indirect labeling saves cost in comparison with the direct labeling.

Embodiment 3: Preparation of Human Chromosome 13 Specific FISH Probe

Embodiment 3 is different from the above Embodiments 1 and 2 in that: the target DNA is from the entire chromosome, random primer is adopted, isothermal amplifying and marking are performed simultaneously, and the doped marker is an indirect marker.

I. Purchase or self-provide (the method is omitted) peripheral blood metaphase lymphocytes of a normal person.

II. The cytogenetic chromosome banding technique is adopted to identify and number chromosomes under a microscope, and ten complete chromosomes 13 are scraped and collected from a slide.

III. Obtaining of a large amount of DNAs: the chromosomes obtained in step II are used as a DNA source, the REPLI-g Single Cell Kit of Qiagen is adopted to perform a large amount of DNA amplification according to the instruction, and the amplified product is purified and recovered by the QIAamp™ DNA Blood Kit of Qiagen.

IV. 1 μg of DNAs obtained in the above step is fragmented by using a focused ultrasonic method and 150-600 bp DNA fragments are recovered. The method is the same as that in Embodiment 1.

V. Enzyme modification processing: the method is the same as that in Embodiment 1.

VI. An adaptor containing a DNA restriction enzyme site sequence is ligated with the recovered DNA fragments after the modification in step V to obtain a DNA probe template. The method is the same as that in Embodiment 1.

VII. Obtaining of a large amount of marked DNAs: the DNA template obtained in step VI is used to perform a large amount of isothermal amplifications while doping the indirect marker aa-dUTP simultaneously, and the 6-base random oligonucleotide (the sequence is NNNNNN, wherein N denotes A or T or G or C) is used as a primer. The reaction system and procedure are as follows (the reaction volume may be increased in proportion):

| DNA probe template | 1 ng; |
| 10 times of buffer solution | 1.5 μl |
| Primer | 50 μM (final concentration in 15 μl) |
| Deionized water | adding up to 15 μl; |

Incubate at 96° C. for 2 minutes, and then at a room temperature for 10 minutes. Thereafter, it is placed on ice, the following components are then added so that the final volume is 50 μl, and mixed well:

| 10 times of buffer solution | 5 μl |
| DMSO | 2 μl |
| BSA | 2 μg |
| dNTP (aa-dUTP:dTTP = 3:1) | 400 μM (final concentration in 50 μl of the reaction system) |
| Bst DNA polymerase large fragments | 20 μ |
| Deionized water | adding up to 50 μl |

Incubate at 60° C. for 6 hours, and then at 80° C. for 15 minutes.

Purify and recover the products with the QIAamp™ DNA Blood Kits of Qiagen. Measure the OD value of the purified DNA.

VIII. The DNAs obtained in step VII are enzyme digested by using a restriction enzyme to obtain 150-600 bp fragments. The method is the same as that in Embodiment 1.

IX. The QIAquick™ PCR Purification Kit of Qiagen is adopted to purify the enzyme digested product. Measure the OD of the purified.

X. Coupling between the aa doped in the DNA and TAMRA™ SE: the method is the same as that in Embodiment 2.

XI. After the product is purified through ethanol precipitation, the OD value is measured and the chromosome 13 specific FISH probe labeled with the orange-red fluorescent TAMRA™ is obtained.

Embodiment 4: Effect Verification Experiment

Agarose gel electrophoresis is performed for the HER2 gene detection FISH probe labeled with orange-red fluorescein TAMRA™ obtained in Embodiment 2, and the result is shown in FIG. 1. FIG. 1 is the result of agarose gel electrophoresis of the obtained HER2 probe, wherein lane 1 is a DNA ladder of 100 bp, and lane 2 is the probe. It shows that the probe length is within the design range of 150-600 bp, meeting the design requirements.

Preparation of HER2 Gene Detection FISH Probe Hybridization Solution

The components of the HER2 gene detection FISH probe hybridization solution per 10 μl are as follows: 20 ng of the HER2 gene detection FISH probe labeled with orange-red fluorescein TAMRA™ obtained in Embodiment 2, 10 ng of chromosome 17 enumeration probe CEN17 obtained in Embodiment 1, 1 μg of human COT-1 DNA (purchased from ThermoFisher Scientific), 50% volume ratio of the deionized formamide, 2×SSC, and 10% weight and volume ratio of dextran sulfate.

Preparation of Chromosome 13 Specific FISH Probe Hybridization Solution

The components of the chromosome 13 specific FISH probe hybridization solution per 10 μl are as follows: 20 ng of the chromosome 13 specific FISH probe labeled with orange-red fluorescein TAMRA™ obtained in Embodiment 3, 1 μg of human COT-1 DNA (purchased from ThermoFisher Scientific), 50% volume ratio of the deionized formamide, 2×SSC, and 10% weight and volume ratio of dextran sulfate.

In-Situ Hybridization:

Chromosome slides are conventionally prepared from metaphase cell suspension. The slide is dehydrated and dried in serial ethanol and digested with pepsin. 10 μl of the above HER2 gene detection FISH probe hybridization solution or chromosome 13 specific FISH probe hybridization solution is added to the hybridization area on slide. It is covered with a coverslip and sealed with rubber water, and is denatured at 78° C. for 5 minutes, and hybridized at 37° C. overnight in a wet box. Then, the slide is washed according to the following sequence: in 4×SSC solution, shaking and rinsing for 5 minutes; in 2×SSC and 0.1% volume ratio of Tween-20 solution, shaking and rinsing for 4×2.5 minutes; in 0.1×SSC solution, shaking and rinsing for 5 minutes; dehydrating and drying in serial ethanol. 20 μl DAPI counterstain is added by droplets to the hybridization area, and it is immediately covered with a coverslip. A suitable filter is selected to observe, photograph and record the results under a fluorescence microscope.

Figure 2:
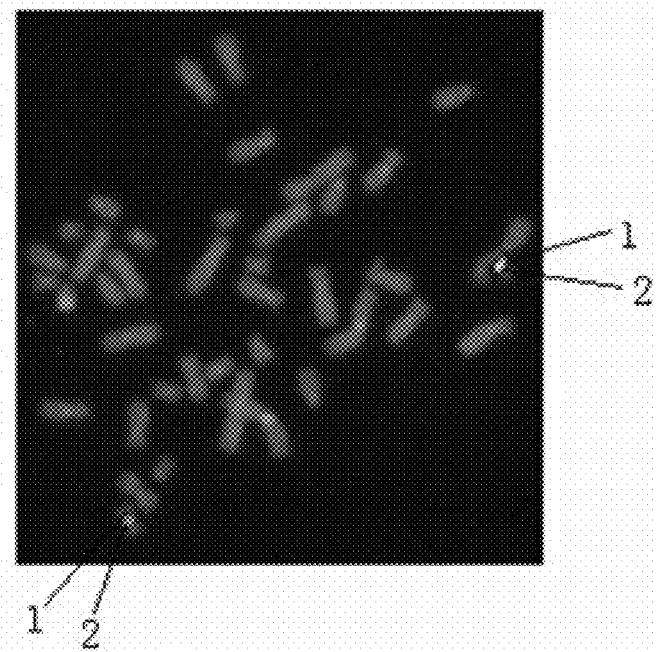
FIG. 2 is a FISH experiment result diagram of the HER2 gene detection FISH probe in Embodiment 2 and CEN 17 in Embodiment 1 on a metaphase cell chromosome of a normal person.
Figure 3:
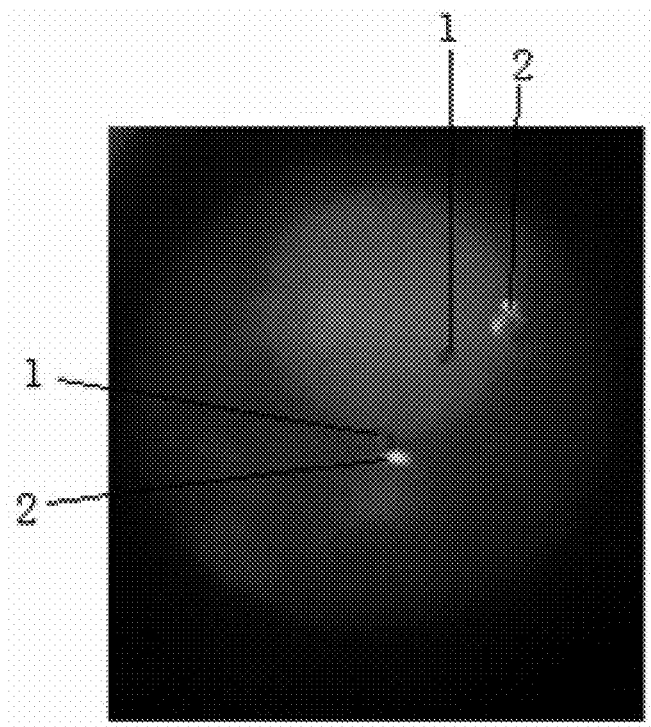
FIG. 3 is a FISH experiment result diagram of the HER2 gene detection FISH probe in Embodiment 2 and CEN 17 in Embodiment 1 on an interphase cell chromosome of a normal person.
Figure 4:
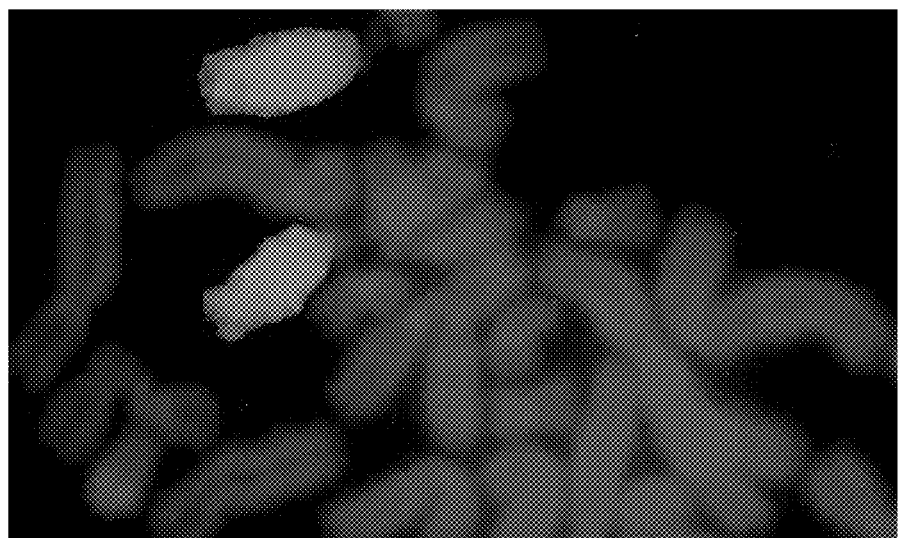
FIG. 4 is a FISH experiment result diagram of a chromosome 13 specific FISH probe in Embodiment 3 on a metaphase cell chromosome of a normal person.

The experiment results are shown in FIGS. 2, 3 and 4. FIG. 2 is a FISH experiment result of the HER2 gene detection FISH probe on chromosome of a metaphase cell (from peripheral blood mononuclear cells) cultured in vitro from a normal person; wherein 1 denotes a signal generated by the HER2 gene detection FISH probe, and 2 denotes a signal generated by the chromosome 17 enumeration in-situ hybridization probe CEN17.

FIG. 3 is a FISH experiment result diagram of the HER2 gene detection FISH probe on an interphase cell (from peripheral blood mononuclear cells) cultured in vitro from a normal person; wherein 1 denotes a signal generated by the HER2 gene detection FISH probe, and 2 denotes a signal generated by the chromosome 17 enumeration in-situ hybridization probe CEN17.

It can be seen from FIGS. 2 and 3 that the CEN17 SIGNAL is located at a centromere of the chromosome 17, and the HER2 signal is located near the centromere of the chromosome 17 (zone 1 and band 2, 17q12). There are two signals in normal cells, meeting the design requirements and expected result.

FIG. 4 is a FISH experiment result of the chromosome 13 specific FISH probe on chromosome of a metaphase cell (from peripheral blood mononuclear cells) cultured in vitro from a normal person, and a pair of the whole chromosomes 13 show fluorescent signals, meeting the design requirements and expected result.

Although the embodiments of the present invention have been shown and described above, it can be understood that the above embodiments are exemplary and should not be understood as limitations to the present invention or as limitations to the application scope of probe products obtained according to the present invention. Those skilled in the field can make changes, modifications, replacements and transformations to the above embodiments within the scope of the present invention without departing from the principle and purpose of the present invention.

What is claimed is:

1. A preparation method for in-situ hybridization probes, comprising the following steps:

fragmenting target DNAs, and recovering 150-600 bp small fragments;

performing an enzyme modification processing on two ends of each of the 150-600 bp small fragments, to make the two ends blunt, then adding phosphate to 5' end and dA to 3' end of each single strand;

ligating the small fragments after processed and DNA adaptors alternately to form large DNA loops and long chains, wherein the adaptor has restriction enzyme site sequences, phosphate at the 5' end and dT at the 3' end of each single strand;

obtaining and labeling the DNAs by:

A, isothermal amplifying, mixing a single nucleotide substrate with a marker when amplifying, to obtain a DNA product with the marker;

or B, isothermal amplifying, and then mixing a nucleotide substrate with a marker to the obtained DNA product by performing a nick translation method or a random primer PCR method, to obtain a DNA product with the marker;

in the step A or B, the marker is a direct marker or an indirect marker;

digesting the DNA product with the marker by using a DNA restriction enzyme corresponding to a base sequence of the above DNA adaptor, wherein a length range of the enzyme digested product is 150-600 bp; and obtaining a probe, wherein if the marker in the DNA product with the marker is the direct marker, the obtained enzyme digested product being the in-situ hybridization probe; and wherein if the marker in the DNA product with the marker is the indirect marker, the obtained enzyme digested product being coupled with the direct marker having corresponding reactivity, thereby obtaining the in-situ hybridization probe.

2. The preparation method for the in-situ hybridization probes of claim 1, wherein the obtained in-situ hybridization probe is further purified and quantified.

3. The preparation method for the in-situ hybridization probes of claim 1, wherein the target DNAs are purified target DNAs.

4. The preparation method for the in-situ hybridization probes of claim 1, wherein in the step A or B, a primer used when isothermal amplifying is an oligonucleotide of an adaptor sequence containing restriction enzyme sites or oligonucleotides of random sequences.

5. The preparation method for the in-situ hybridization probes of claim 1, wherein in the step A or B, an enzyme used when isothermal amplifying is a DNA polymerase having chain replacement activity.

6. The preparation method for the in-situ hybridization probes of claim 5, wherein an enzyme used when isothermal amplifying is Phi29 DNA polymerase or Bst DNA polymerase large fragments.

* * * * *